US00PP14460P29

(12) United States Plant Patent
Heims

(10) Patent No.: US PP14,460 P2
(45) Date of Patent: Jan. 13, 2004

(54) PODOPHYLLUM PLANT NAMED 'KALEIDOSCOPE'

(50) Latin Name: *Podophyllum hybrid*
Varietal Denomination: Kaleidoscope

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 0 days.

(21) Appl. No.: 10/213,614

(22) Filed: Aug. 6, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct Podophyllum plant characterized by beautiful large umbrella-like leaves with a kaleidoscope pattern in shades of bronze, silver, and green.

3 Drawing Sheets

Latin name of the genus and species of the plant claimed: *Podophyllum hybrid.*

Variety denomination: 'Kaleidoscope'.

The present invention relates to a new and distinct cultivar of *Podophyllum hybrid* and given the cultivar name 'Kaleidoscope'. Podophyllum is in the family Berberidaceae.

This new cultivar originated from a cross between *Podophyllum hybrid* 374 (an unpatented proprietary plant) as the seed parent and *Podophyllum hybrid* 352 (an unpatented proprietary plant) as the pollen parent. These two *Podophyllum hybrids* are outstanding selections out of a hybrid swarm in a Japanese nursery, which I believe come from *P. difforme, P. delavayi,* and *P. versipelle.* The new cultivar was chosen for its outstanding foliage and vigor.

This plant is characterized by the following:

1. Beautiful large umbrella shaped leaves with a kaleidoscope look of color and pattern.
2. Two leaves per crown that will increase in size with maturity to 40 cm wide.
3. Numerous large maroon flowers with maturity.
4. Excellent vigor.

This new cultivar has been reproduced only by asexual propagation (tissue culture). Each of the progeny exhibits identical characteristics to the original plant. Asexual propagation by tissue culture using standard micropropagation techniques with side shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
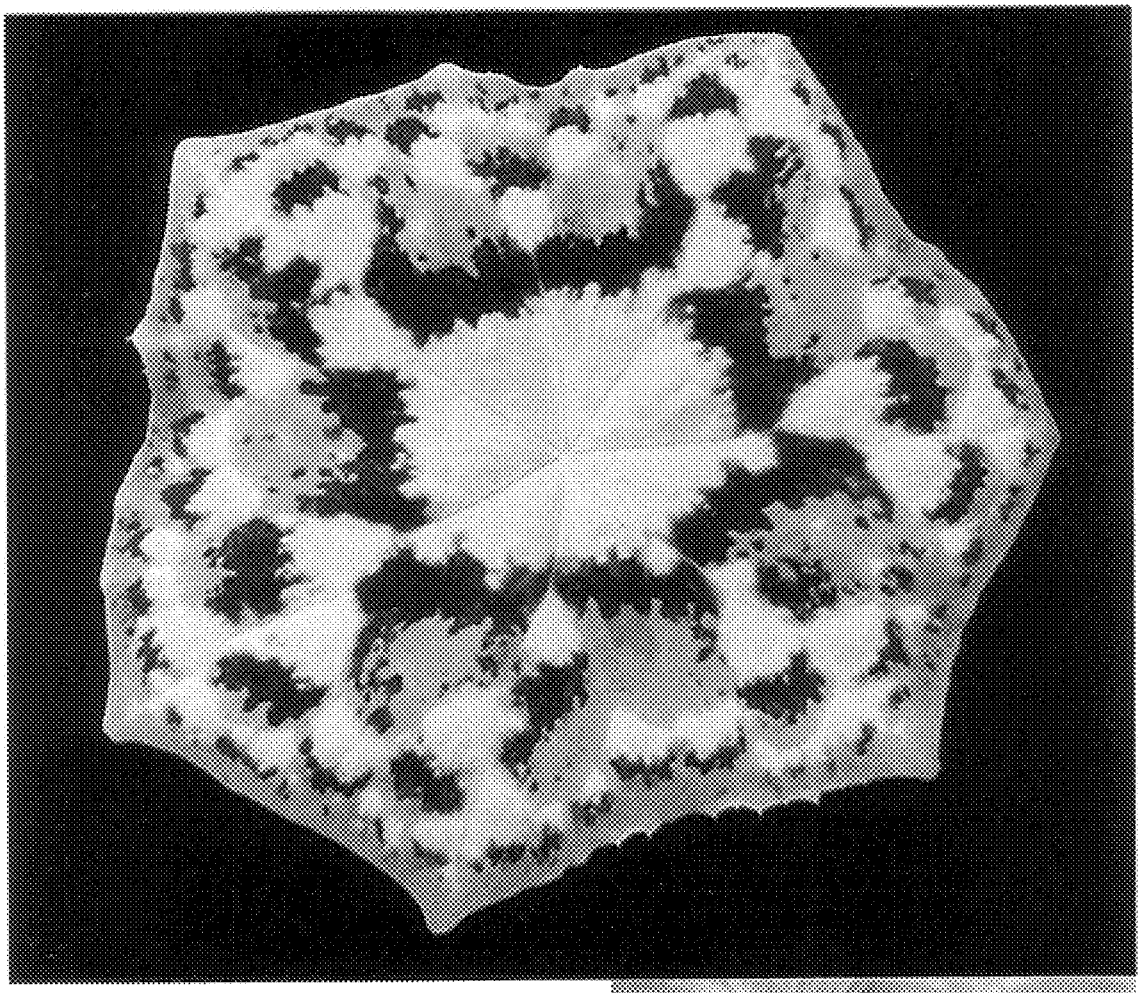
FIG. 1 shows one leaf in spring of a two-year-old Podophyllum 'Kaleidoscope' grown in a one-gallon container in a cool greenhouse.
Figure 2:
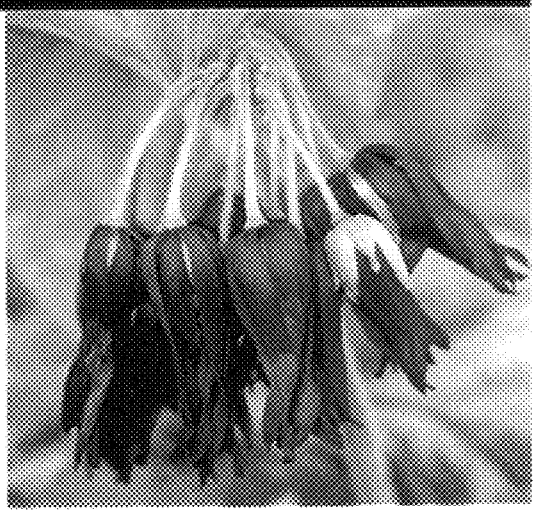
FIG. 2 shows the flowers of the six-year-old parent plants.
Figure 3:
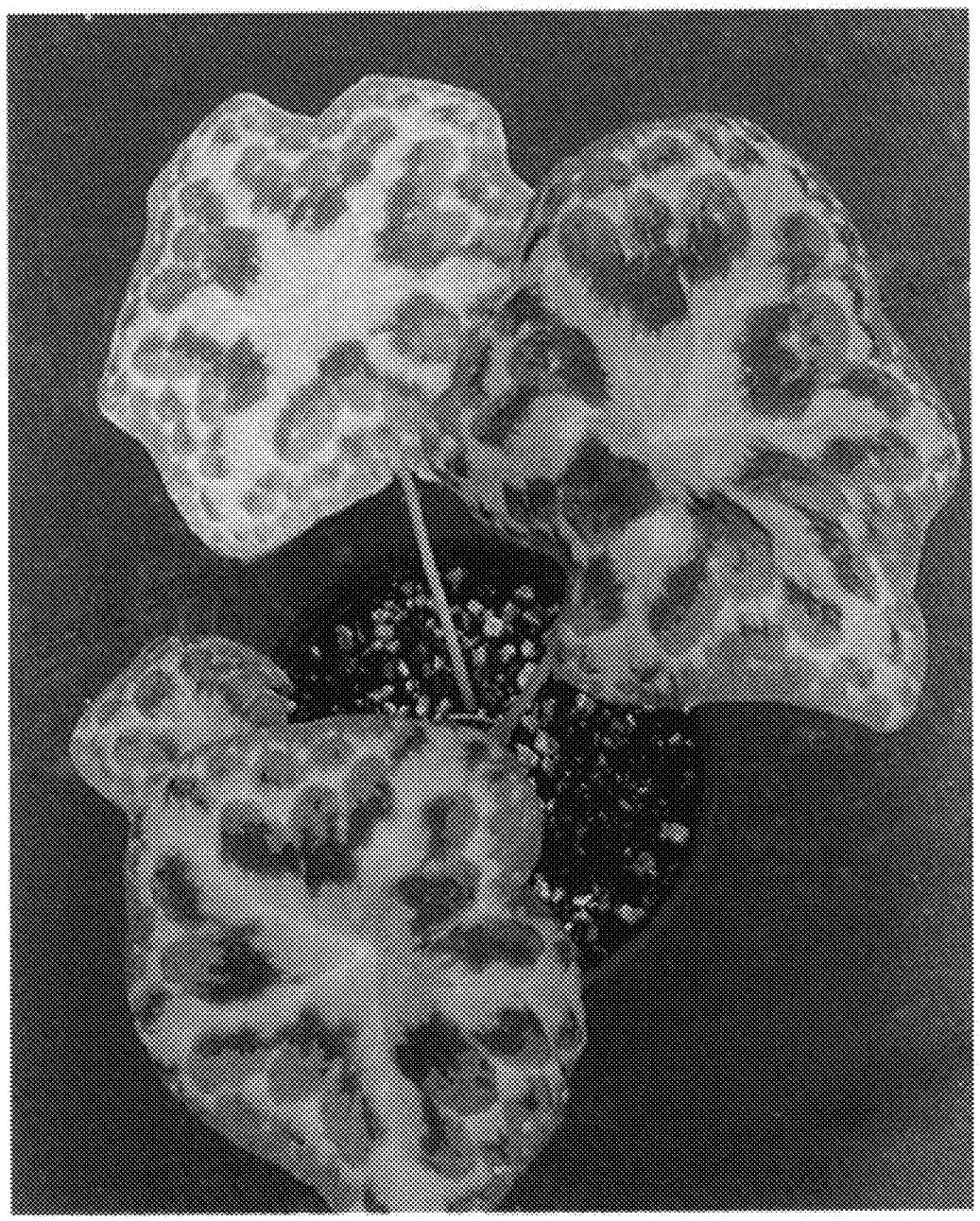
FIG. 3 shows a two-year-old whole plant in July grown in a cool greenhouse in one-gallon pot in Canby, Oreg.
Figure 4:
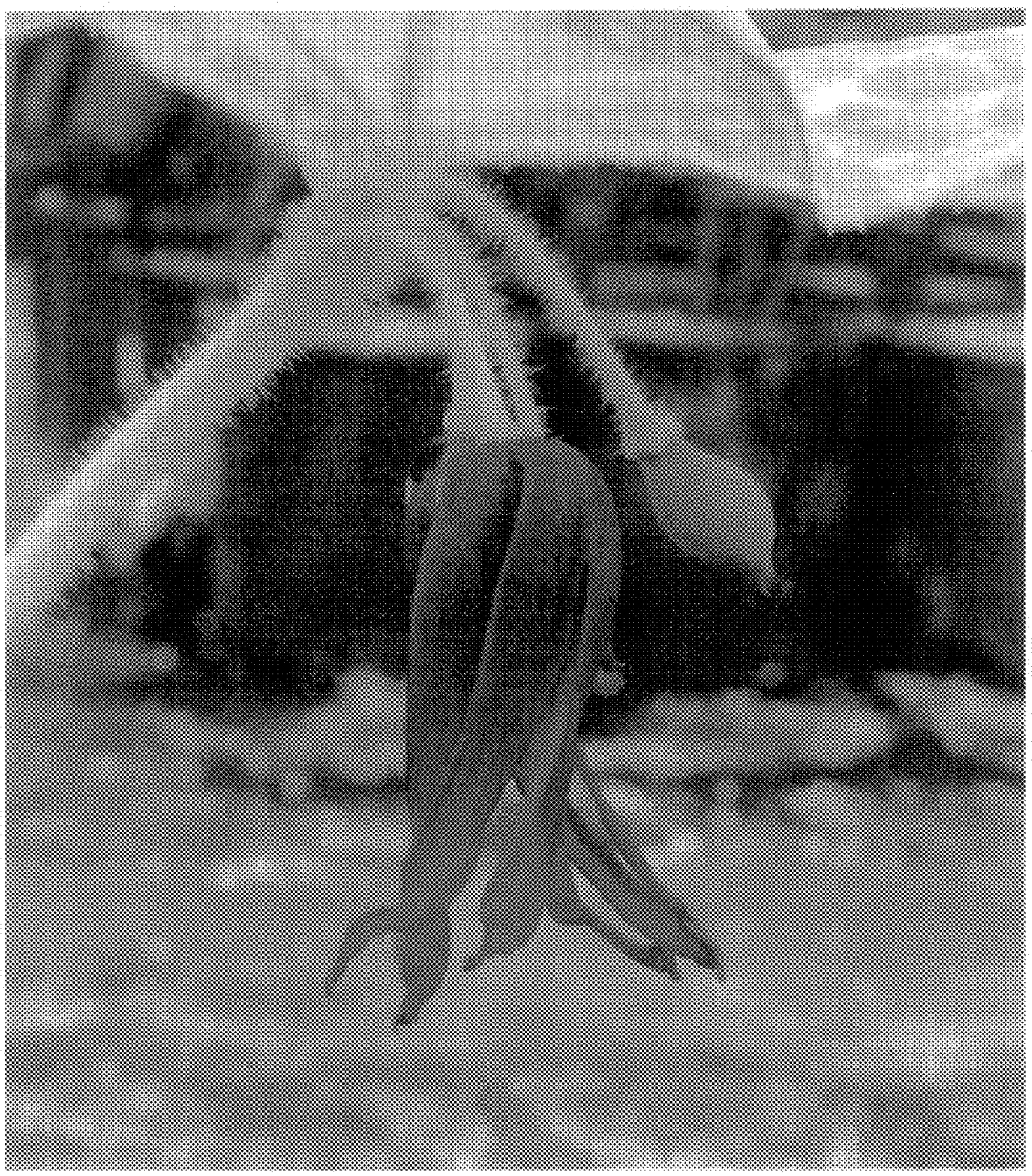
FIG. 4 shows a flower of Podophyllum 'Kaleidoscope'.

The following is a detailed description of the new Podophyllum cultivar based on observations of the foliage of two-year-old specimens grown in the greenhouse in one-gallon containers and the flowers of the five year old parent plants grown in five-gallon containers in Canby, Oreg. The color descriptions are all based on The Royal Horticultural Society Colour Chart.

Botanical classification: *Podophyllum hybrid.*
Cultivar name: 'Kaleidoscope'.

Plant:
- *Type.*—Herbaceous perennial.
- *Form.*—Stoutly rhizomatous, with two leaves per crown.
- *Hardiness.*—U.S.D.A. Hardiness Zones 6–9.
- *Size.*—10 cm tall and 29 cm wide. Six-year-old mother plants grew to 70 cm tall and 150 cm wide, with 10 crowns.

Stem:
- *Type.*—Annual erect, unbranched aerial stems.
- *Size.*—6 mm wide.
- *Vestiture.*—Pubescent, with many long soft hairs.
- *Color.*—Yellow Green 144A.

Leaf:
- *Type.*—Simple.
- *Arrangement.*—Alternate.
- *Shape.*—Irregularly or regularly peltate, pentagonal to octagonal in appearance. With age leaves have pronounced lobes.
- *Blade size.*—17 to 28 cm wide.
- *Venation.*—Palmate.
- *Margins.*—More or less revolute and irregularly toothed.
- *Apices.*—Mucronulate.
- *Base.*—Leaf dips in where connected to petiole.
- *Texture.*—Leathery.
- *Vestiture.*—Glabrous on top and pubescent on bottom.
- *Petiole.*—Length — 18 cm for terminal leaf and 17 cm for lower leaf. Width — Grows to 1 cm. Vestiture — Pubescent with many long soft hairs. Color — Yellow Green 144A.

*Leaf color.*—Varies with light, temperature and age. Best leaf color occurs with high light, cool temperatures and young leaves. Abaxial — Leaf center and along veins is silvery, Yellow Green 145B and C and 146C. Around the leaf center and in between the veins it has brown blotches, Greyed Purple 187A to Greyed Brown 166A. The rest of the leaf is of green shades, Yellow Green 146A and B and 147B. The brown colors fade over time. Adaxial — Yellow Green 147C.

Inflorescence: Borne at the end of the petiole at the base of the terminal leaf.

*Number and type.*—13 to 20 in one to two umbel-like groups, pendulous.

*Size.*—6 to 9 cm wide and 10 to 12 cm deep.

*Pedicel.*—Length — 5.7 cm. Vestiture — Pubescent. Color — Yellow Green 146C.

*Bloom time.*—Spring.

Flower bud:

*Size.*—2 cm. wide and 5.5 cm. deep.

*Description.*—Upside down teardrop shape, imbricate.

*Color.*—Greyed Purple 187A, but blacker.

Flower:

*Type.*—Actinomorphic, bisexual, and pendulous.

*Size.*—2.5 cm wide and 6 cm deep.

*Color.*—Dark red-purple, Greyed Purple 187A but blacker on bottom half and tip.

*Petal number.*—6.

*Petal size.*—1.2 cm wide and 6 cm deep.

*Petal shape.*—Lanceolate with a rounded irregular apex.

*Petal vestiture.*—Glabrous.

*Calyx.*—Fugacious, imbricate. Sepal number — 3. Size — 0.9 cm wide and 0.3 cm. deep. Vestiture — Pubescent. Color — Only seen dried and then was Greyed-Yellow, 160A.

*Stamens.*—Number — 6. Size — 16 mm long and 2.8 mm wide. Filaments — 1 cm long and 2 mm wide, color is between Black 202A and Greyed Purple 187A. Anthers — Oblong. Brown 200A before dehiscence. Anther mucro is 0.45 cm long. Pollen — Yellow 10B.

*Pistil.*—13.3 cm long. Ovary superior.

*Stigma.*—Large, 0.3 by 0.3 cm, convoluted, Greyed Yellow 161A and inside Greyed Orange 176B.

*Fragrance.*—Poor, fly pollinated.

Fruit:

*Type.*—Spherical, fleshy berry.

*Fertiliy.*—Self-incompatible.

*Color.*—Green 138A, when mature and glaucous.

Seed:

*Shape.*—Round and flat.

*Size.*—3 mm wide.

*Color.*—Tan, Yellow White 158A.

Disease: None observed on plants grown commercially in Canby, Oreg.

COMPARISONS

This new cultivar was selected and compared to the less colored and unpatented proprietary parent plants. The parent plants were selected from a large population of well-marked plants. Podophyllum 'Kaleidoscope' has been shown to have much superior leaf markings and colorings.

I claim:

1. A new and distinct variety of Podophyllum plant substantially as shown and described.

* * * * *